United States Patent
Huang

(10) Patent No.: US 11,662,567 B2
(45) Date of Patent: May 30, 2023

(54) IMAGE CAPTURING ASSEMBLY AND RELATED ENDOSCOPE

(71) Applicant: ALTEK BIOTECHNOLOGY CORPORATION, Hsinchu (TW)

(72) Inventor: Yu-Cheng Huang, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 71 days.

(21) Appl. No.: 17/395,481

(22) Filed: Aug. 6, 2021

(65) Prior Publication Data

US 2023/0042245 A1 Feb. 9, 2023

(51) Int. Cl.
*G02B 23/24* (2006.01)
*H04N 23/54* (2023.01)
*H04N 23/55* (2023.01)
*H05K 1/18* (2006.01)
*H04N 23/50* (2023.01)

(52) U.S. Cl.
CPC ......... *G02B 23/2484* (2013.01); *H04N 23/54* (2023.01); *H04N 23/55* (2023.01); *H05K 1/189* (2013.01); *G02B 23/243* (2013.01); *H04N 23/555* (2023.01); *H05K 2201/10121* (2013.01)

(58) Field of Classification Search
CPC .............. G02B 23/2484; G02B 23/243; H04N 5/2253; H04N 5/2254; H04N 2005/2255; H05K 1/189; H05K 2201/10121
USPC .......................................................... 348/65
See application file for complete search history.

(56) References Cited

U.S. PATENT DOCUMENTS

| | | | |
|---|---|---|---|
| 8,194,121 B2 | 6/2012 | Blumzvig | |
| 8,633,429 B2 | 1/2014 | Eismann | |
| 2015/0271370 A1 | 9/2015 | Henley | |
| 2016/0029879 A1 | 2/2016 | Ishikawa | |
| 2016/0072989 A1* | 3/2016 | Kennedy, II | A61B 1/051 348/76 |
| 2018/0049628 A1* | 2/2018 | Motohara | H04N 5/2251 |
| 2018/0070803 A1 | 3/2018 | Mikami | |
| 2020/0221598 A1* | 7/2020 | Loo | H05K 1/184 |
| 2021/0106212 A1 | 4/2021 | Avron | |

FOREIGN PATENT DOCUMENTS

| | | | | |
|---|---|---|---|---|
| CN | 211152328 U | * | 7/2020 | G02B 23/00 |
| CN | 112438689 A | | 3/2021 | |
| DE | 4240454 A1 | * | 6/1994 | H01R 13/33 |

(Continued)

*Primary Examiner* — Behrooz M Senfi
(74) *Attorney, Agent, or Firm* — Winston Hsu

(57) ABSTRACT

An image capturing assembly is provided and includes an image sensing device, a first circuit board, a second circuit board and a lens assembly. The image sensing device includes an electrical connecting component. The first circuit board includes a first contact. The image sensing device is mounted on the first circuit board, and the electrical connecting component is electrically connected to the first contact. The second circuit board includes a second contact. The second circuit board is affixed with the first circuit board and perpendicular to the first circuit board, and the second contact is electrically connected to the first contact, so that the second contact is electrically connected to the electrical connecting component by the first contact. The lens assembly is assembled with the image sensing device. Furthermore, a related endoscope is provided.

15 Claims, 9 Drawing Sheets

(56) References Cited

FOREIGN PATENT DOCUMENTS

| EP | 3170443 B1 | 1/2019 | | |
|---|---|---|---|---|
| TW | 200810727 | 3/2008 | | |
| TW | M603741 U | 11/2020 | | |
| WO | WO-2016203797 A1 * | 12/2016 | ........... | A61B 1/0011 |
| WO | 2017/067491 A1 | 4/2017 | | |
| WO | WO-2017067491 A1 * | 4/2017 | ............. | G02B 23/24 |
| WO | WO-2020181661 A1 * | 9/2020 | ............. | A61B 1/005 |

\* cited by examiner

IMAGE CAPTURING ASSEMBLY AND RELATED ENDOSCOPE

BACKGROUND OF THE INVENTION

1. Field of the Invention

The present invention relates to an image capturing assembly and a related image capturing apparatus, and more specifically, to an image capturing assembly with compact structure and small size and a related endoscope.

2. Description of the Prior Art

An endoscopy is a medical procedure in which an endoscope is inserted into a patient's body to allow a surgeon to inspect an interior of the patient's body. The endoscopy has gained broad acceptance because it only needs a small incision for insertion of the endoscope. However, since the conventional endoscope still has a bulky image capturing assembly, a size of the incision cannot be further reduced in order for insertion of the endoscope with such a bulky image capturing assembly. Therefore, an improvement is required.

SUMMARY OF THE INVENTION

It is an objective of the present invention to provide an image capturing assembly with compact structure and small size and a related endoscope for solving the aforementioned problem.

In order to achieve the aforementioned objective, the present invention discloses an image capturing assembly. The image capturing assembly includes an image sensing device, a first circuit board, a second circuit board and a lens assembly. The image sensing device includes at least one electrical connecting component. The first circuit board includes at least one first contact. The image sensing device is mounted on the first circuit board, and the at least one electrical connecting component is electrically connected to the at least one first contact. The second circuit board includes at least one second contact. The second circuit board is affixed with the first circuit board and perpendicular to the first circuit board, and the at least one second contact is electrically connected to the at least one first contact, so that the at least one second contact is electrically connected to the at least one electrical connecting component by the at least one first contact. The lens assembly is assembled with the image sensing device.

In order to achieve the aforementioned objective, the present invention further discloses an endoscope. The endoscope includes a flexible tube and the image capturing assembly of any one of the aforementioned embodiments, and the image capturing assembly is connected to the flexible tube.

In summary, the present invention utilities the first circuit board for mounting the image sensing device and further utilizes the second circuit board affixed with and substantially perpendicular to the first circuit board for establishing an electrical connection between the second contact of the second circuit board and the electrical connecting component via the first contact of the first circuit board. The aforementioned configuration of the present invention is space-saving. Therefore, the present invention has advantages of compact structure and small size. Besides, when there are a plurality of electrical connecting components, a plurality of first contacts and a plurality of second contacts, the electrical connecting components of the image sensing device can be electrically connected to the second contacts of the second circuit board by the first contacts of the first circuit board respectively, wherein a layout or an arrangement of the electrical connecting components is different from a layout or an arrangement of the second contacts. Therefore, it facilitates adaptation and modularization.

These and other objectives of the present invention will no doubt become obvious to those of ordinary skill in the art after reading the following detailed description of the preferred embodiment that is illustrated in the various figures and drawings.

DETAILED DESCRIPTION

In the following detailed description of the preferred embodiments, reference is made to the accompanying drawings which form a part hereof, and in which is shown by way of illustration specific embodiments in which the invention may be practiced. In this regard, directional terminology, such as "top", "bottom", "front", "back", etc., is used with reference to the orientation of the Figure(s) being described. The components of the present invention can be positioned in a number of different orientations. As such, the directional terminology is used for purposes of illustration and is in no way limiting. Accordingly, the drawings and descriptions will be regarded as illustrative in nature and not as restrictive. Also, the term "connect" is intended to mean either an indirect or direct electrical/mechanical connection. Thus, if a first device is connected to a second device, that connection may be through a direct electrical/mechanical connection, or through an indirect electrical/mechanical connection via other devices and connections.

Figure 1:
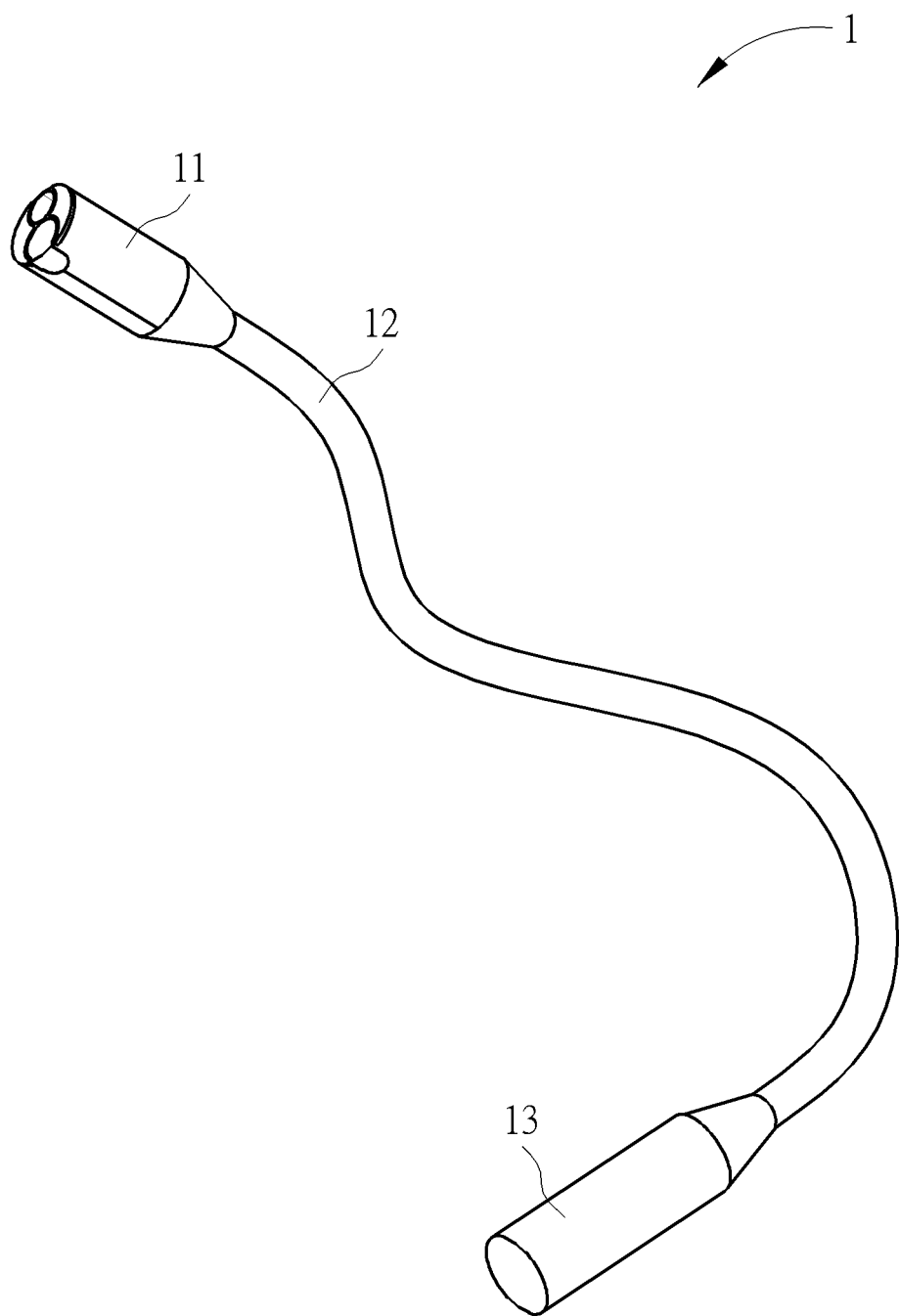
FIG. 1 is a schematic diagram of an endoscope according to an embodiment of the present invention.

Please refer to FIG. 1. FIG. 1 is a schematic diagram of an endoscope 1 according to an embodiment of the present invention. As shown in FIG. 1, the endoscope 1 includes an image capturing assembly 11, a flexible tube 12 and a handle 13. The image capturing assembly 11 is for capturing images. The handle 13 is for hand-holding and can be provided with a control console for at least controlling the image capturing assembly 11. The flexible tube 12 is connected between the image capturing assembly 11 and the handle 13.

Figure 2:
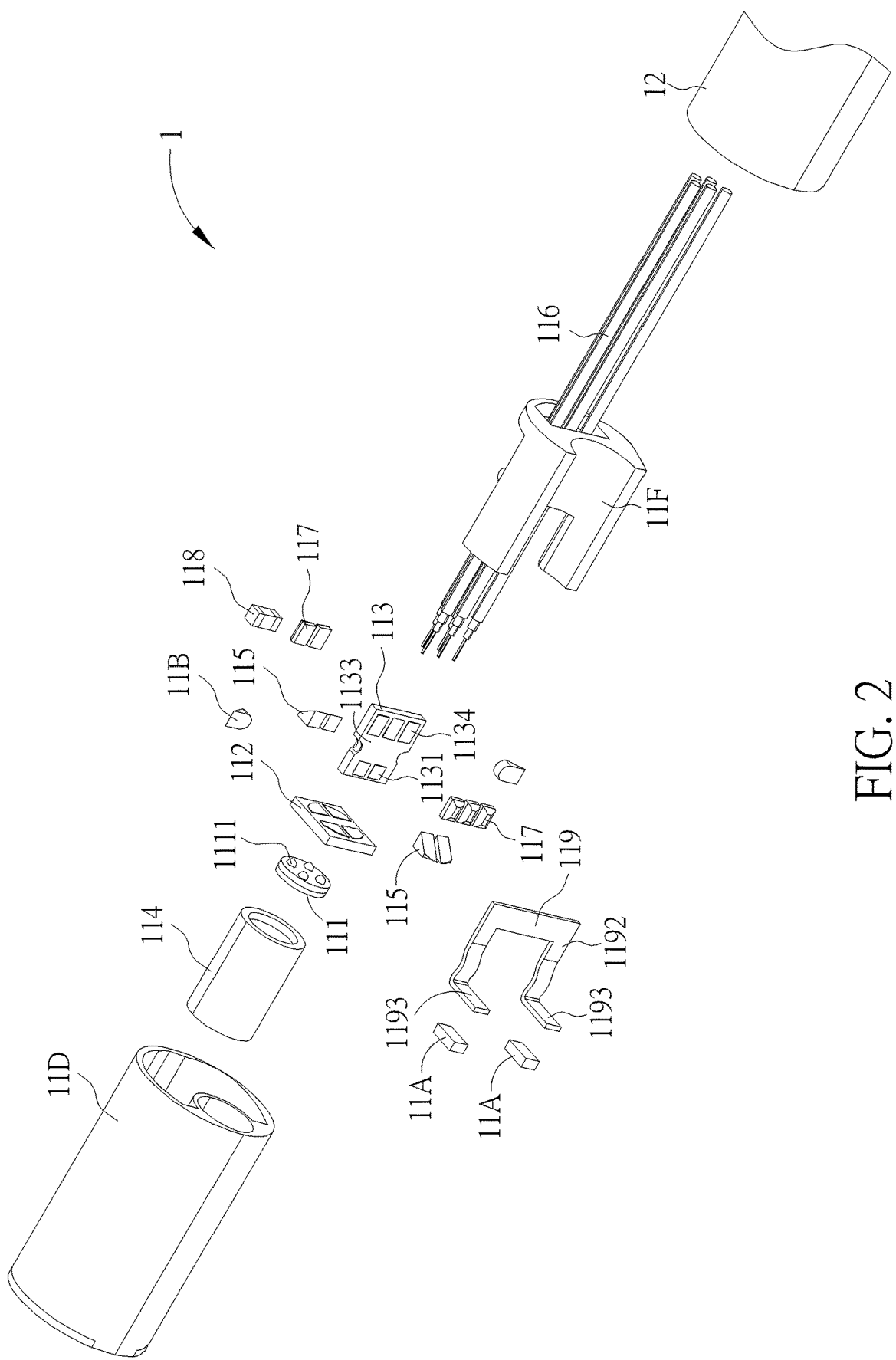
FIG. 2 and FIG. 3 are partial exploded diagrams of the endoscope at different views according to the embodiment of the present invention.
Figure 3:
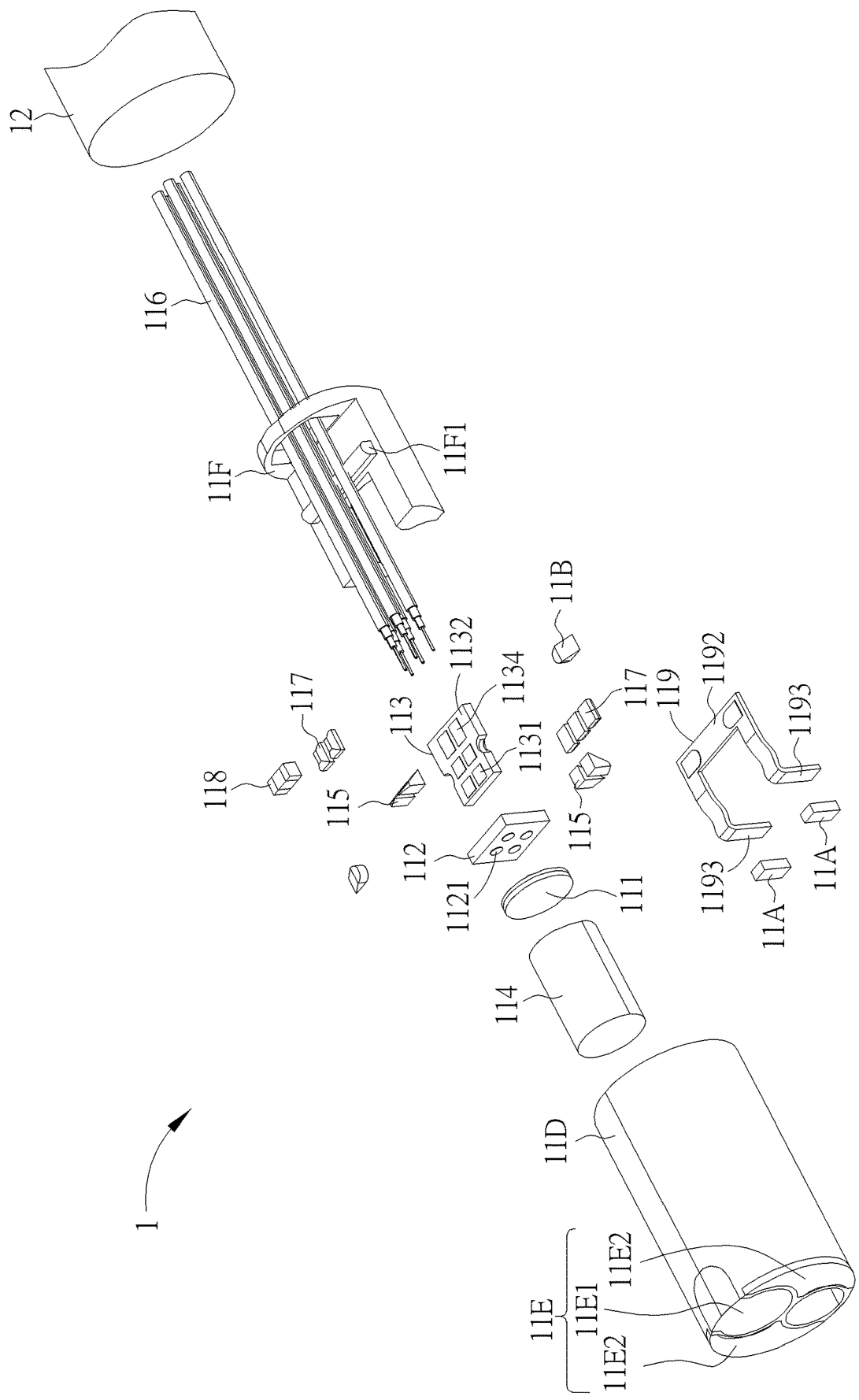
Figure 4:
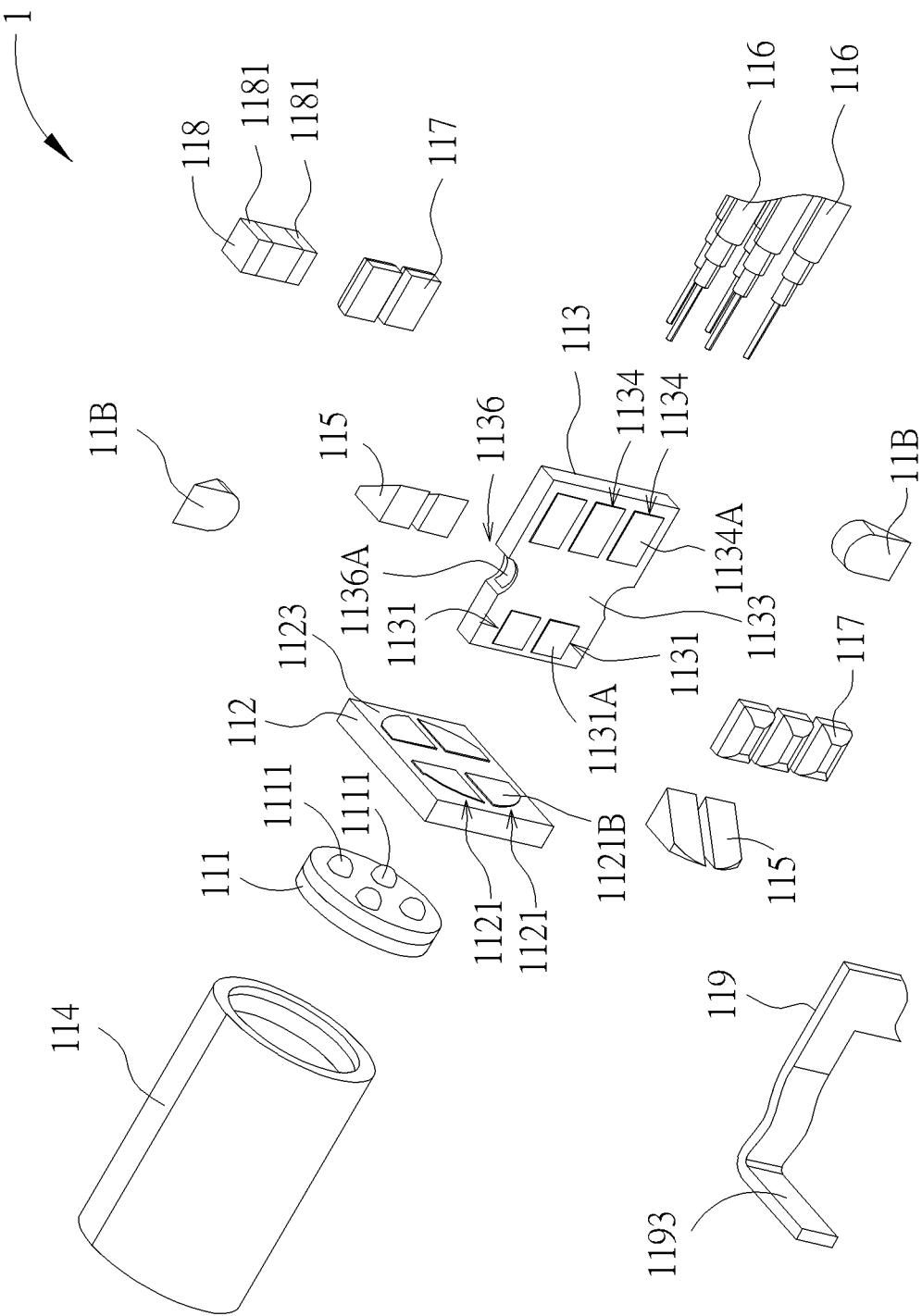
FIG. 4 is a partial enlarged diagram of the endoscope shown in FIG. 2 according to the embodiment of the present invention.
Figure 5:
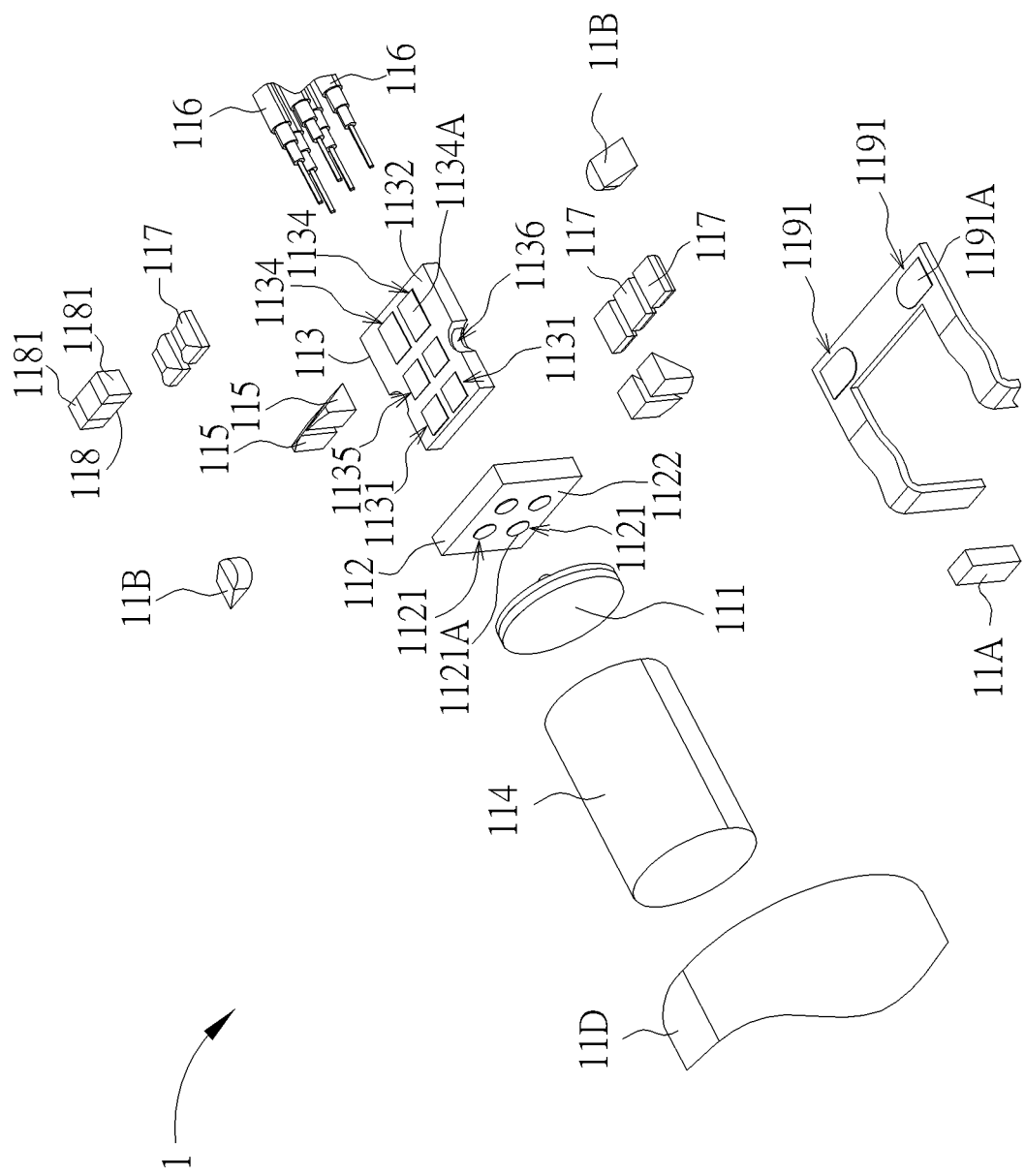
FIG. 5 is a partial enlarged diagram of the endoscope shown in FIG. 3 according to the embodiment of the present invention.
Figure 6:
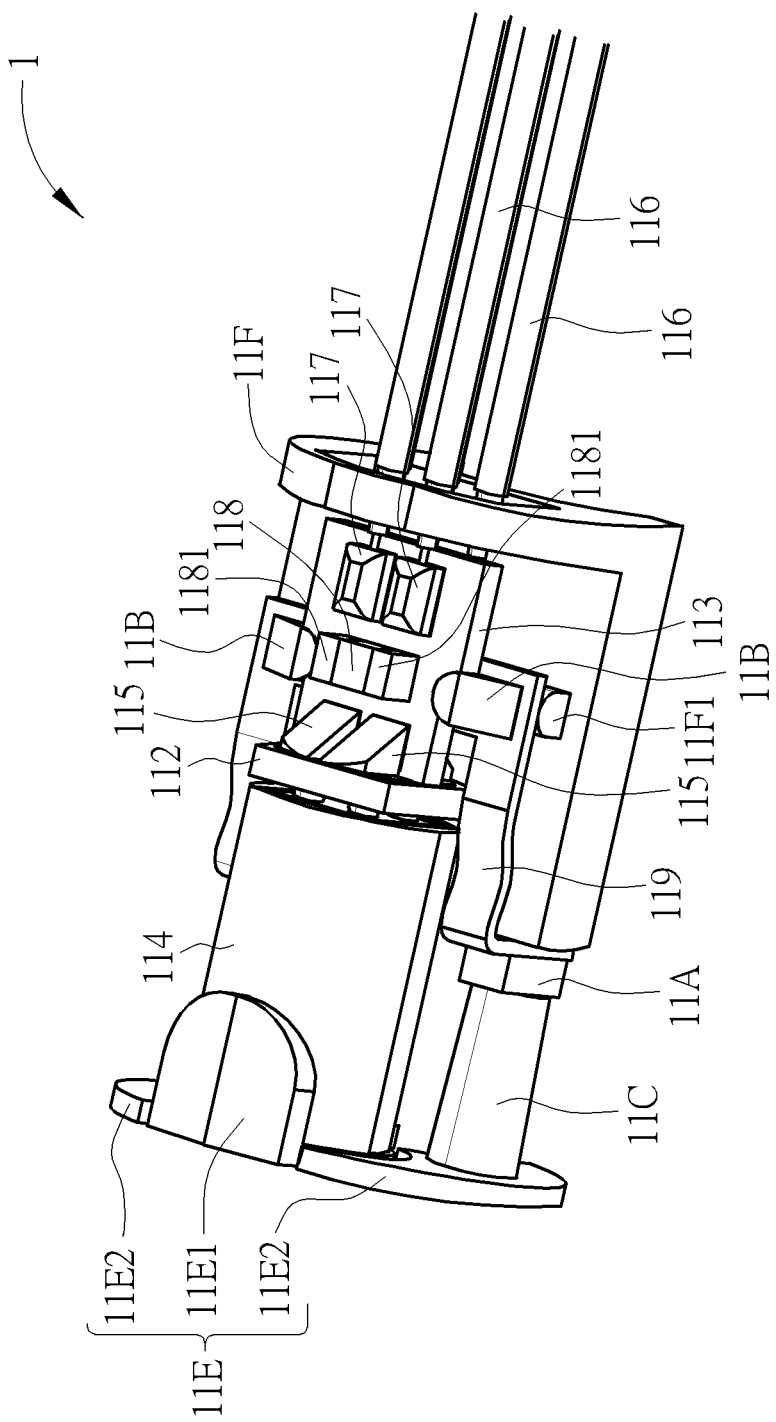
FIG. 6 and FIG. 7 are partial internal structural diagrams of the endoscope at different views according to the embodiment of the present invention.
Figure 7:
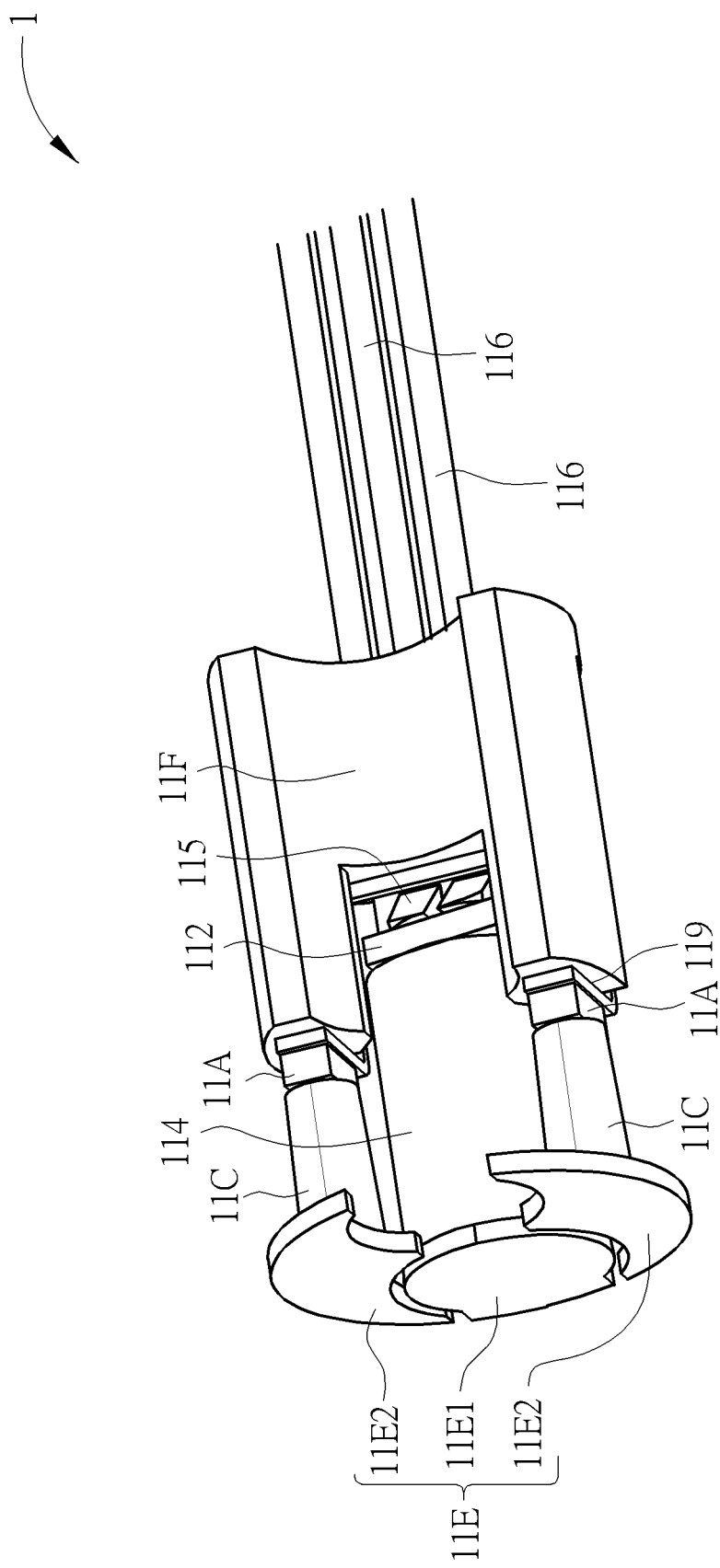

Please further refer to FIG. 2 to FIG. 7. FIG. 2 and FIG. 3 are partial exploded diagrams of the endoscope 1 at different views according to the embodiment of the present invention. FIG. 4 is a partial enlarged diagram of the endoscope 1 shown in FIG. 2 according to the embodiment of the present invention. FIG. 5 is a partial enlarged diagram of the endoscope 1 shown in FIG. 3 according to the embodiment of the present invention. FIG. 6 and FIG. 7 are partial internal structural diagrams of the endoscope 1 at different views according to the embodiment of the present invention. As shown in FIG. 2 to FIG. 7, the image capturing assembly 11 is located at a distal end of the flexible tube 12 away from the handle 13 and includes an image sensing device 111, e.g., a CMOS sensor, a first circuit board 112, a second circuit board 113 and a lens assembly 114.

In this embodiment, the image sensing device 111 includes four electrical connecting components 1111. The first circuit board 112 includes four first contacts 1121. The image sensing device 111 is mounted on the first circuit board 112, and each of the electrical connecting components 1111 is electrically connected to the corresponding first contact 1121. The second circuit board 113 includes four second contacts 1131. The second circuit board 113 is affixed with the first circuit board 112 and substantially perpendicular to the first circuit board 112, and each of the second contacts 1131 is electrically connected to the corresponding first contact 1121, so that each of the second contacts 1131 is electrically connected to the corresponding electrical connecting component 1111 by the corresponding first contact 1121. The electrical connecting components 1111 of the image sensing device 111 can be electrically connected to the second contacts 1131 of the second circuit board 113 by the first contacts 1121 of the first circuit board 112 respectively, wherein a layout or an arrangement of the electrical connecting components 1111 is different from a layout or an arrangement of the second contacts 1131. Therefore, it facilitates adaptation and modularization. The lens assembly 114 is assembled with the image sensing device 111 and can be a fixed focus length lens assembly or can be a zoom lens assembly configured to zoom in or zoom out a view of the image sensing device 111.

However, the numbers of the electrical connecting component, the first contact and the second contact are not limited to this embodiment. It depends on practical demands. For example, in another embodiment, there can be only one electrical connecting component, one first contact and one second contact electrically connected to one another.

Specifically, each of the first contacts 1121 can include a first pad portion 1121A exposed on a first side 1122 of the first circuit board 112 and a second pad portion 1121B exposed on a second side 1123 of the first circuit board 112 opposite to the first side 1122 of the first circuit board 112 and aligned with the first pad portion 1121A. The image sensing device 111 can be a surface mounted device mounted on the first side 1122 of the first circuit board 112, and each of the electrical connecting components 1111 can be a solder ball which is affixed with the first pad portion 1121A of the corresponding first contact 1121 by soldering, so as to establish an electrical connection of the corresponding electrical connecting component 1111 and the corresponding first contact 1121. Furthermore, each of the two the second contacts 1131 can include a third pad portion 1131A. Two of the third pad portions 1131A can be exposed on a third side 1132 of the second circuit board 113, and the other two of the third pad portions 1131A can be exposed on a fourth side 1133 of the second circuit board 113 opposite to the third side 1132 of the second circuit board 113. Each of the third pad portions 1131A and the corresponding second pad portions 1121B do not contact with each other directly.

Each of the third pad portions 1131A can be perpendicular to the corresponding second pad portions 1121B and affixed with the corresponding second pad portion 1121B by soldering, so as to establish an electrical connection of the corresponding second contact 1131 and the corresponding first contact 1121, i.e., the image capturing assembly 11 can further include four first soldering structures 115, and each of the first soldering structures 115 is connected between the corresponding second pad portion 1121B and the corresponding third pad portion 1131A.

However, the present invention is not limited to this embodiment. For example, in another embodiment, there can be only one electrical connecting component, one first contact having one first pad portion and one second pad portion exposed on the first side and the second side of the first circuit board respectively but not aligned with first pad portion, and one second contact having one third pad portion exposed on a corresponding side of the second circuit board and directly contacting with the second pad portion. Alternatively, in another embodiment, the second pad portion of the first contact and the third pad portion of the second contact can be inclined relative to each other and affixed with each other by soldering. Alternatively, in another embodiment, the image sensing device can be a surface mounted device whose electrical connecting components can be protruding pins or flat pads, and each of the first contacts can include a cooperating socket portion or a cooperating pin portion for cooperating with the corresponding protruding pin or the corresponding flat pad. Alternatively, in another embodiment, the image sensing device can be a Dual-In line Package (DIP) device whose electrical connecting components can be inserting pins, and each of the first contacts can include a cooperating hole portion for cooperating with the inserting pin.

Besides, as shown in FIG. 2 to FIG. 7, in this embodiment, the image capturing assembly 11 further includes five cables 116 passing through the flexible tube 12 and electrically connected to the second circuit board 113 and a circuit board of the control console of the handle 13, which is not shown in the figures, for providing power and signal transmission between the second circuit board 113 and the circuit board of the control console of the handle 13.

Furthermore, in this embodiment, the second circuit board 113 further includes five third contacts 1134. Each of the cables 116 is electrically connected to the corresponding third contact 1134. Each of the second contacts 1131 is electrically connected to the corresponding third contact 1134, so that each of the electrical connecting components 1111 is electrically connected to the corresponding cable 116 by the corresponding first contact 1121, the corresponding second contact 1131 and the corresponding third contact 1134.

Specifically, each of the third contacts 1134 can include a fourth pad portion 1134A. Two of the fourth pad portions 1134A can be exposed on the third side 1132 of the second circuit board 113, and the other three of the fourth pad portions 1134A can be exposed on the fourth side 1133 of the second circuit board 113. Each of the second contacts 1131 can be electrically connected to the corresponding third contact 1134 by an electrical conducting component, e.g., a wire or a copper layer, so as to establish an electrical connection of the corresponding second contact 1131 and the corresponding third contact 1134. Each of the cables 116 can be affixed with the fourth pad portion 1134A of the corresponding third contact 1134 by soldering, so as to establish an electrical connection of the corresponding cable 116 and the corresponding third contact 1134, i.e., the image capturing assembly 11 can further include five second soldering structures 117 separated from each other, and each of the second soldering structures 117 is connected between the corresponding cable 116 and the corresponding fourth pad portion 1134A.

However, the numbers and the structure of the cable and the third contact are not limited to this embodiment. It depends on practical demands. For example, in another embodiment, there can be only one cable and one third contact, and the third contact can include an inserting portion for insertion of the cable.

Figure 8:
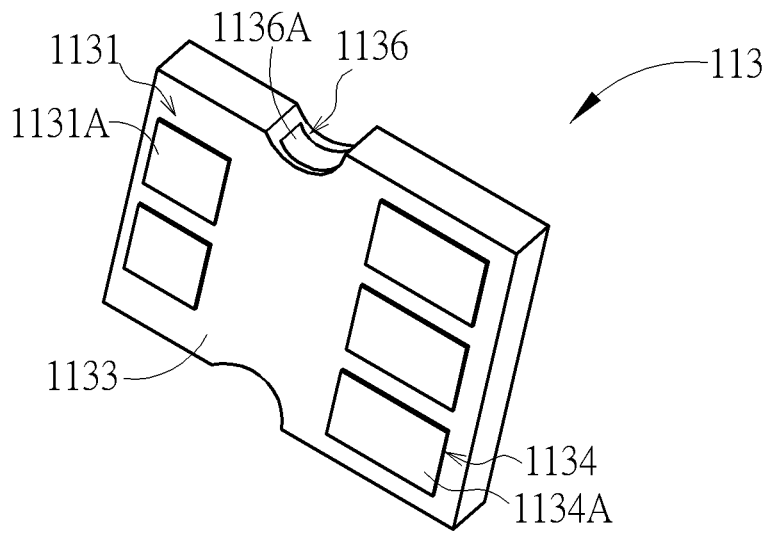
FIG. 8 and FIG. 9 are diagrams of a second circuit board at different views according to the embodiment of the present invention.
Figure 9:
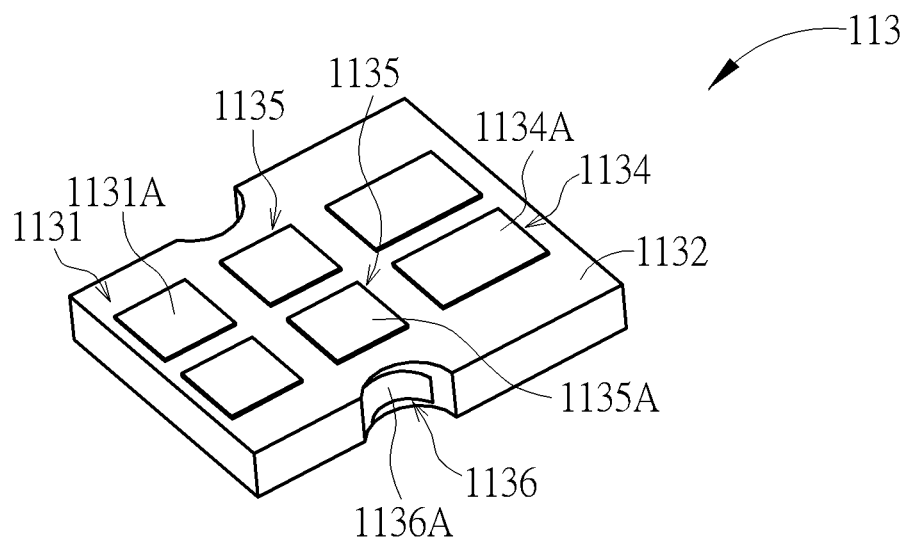

Please refer to FIG. 2 to FIG. 9. FIG. 8 and FIG. 9 are diagrams of the second circuit board 113 at different views according to the embodiment of the present invention. As shown in FIG. 2 to FIG. 9, in this embodiment, the image capturing assembly 11 further includes a passive electronic component 118, e.g., a capacitor or a resistor, electrically connected to the second circuit board 113.

Specifically, the passive electronic component 118 can include two first cooperating contacts 1181. The second circuit board 113 can include two first auxiliary contacts 1135. Each of the two first auxiliary contacts 1135 can include a fifth pad portion 1135A exposed on the fourth side 1133 of the second circuit board 113. Each of the first cooperating contacts 1181 can be affixed with and electrically connected to the fifth pad portion 1135A of the corresponding first auxiliary contact 1135 by soldering, so as to establish an electrical connection of the corresponding first cooperating contacts 1181 and the corresponding first auxiliary contacts 1135, i.e., the image capturing assembly 11 can further include two third soldering structures, which are not shown in the figures, and each of the third soldering structures is connected between the corresponding fifth pad portion 1135A and the corresponding first cooperating contact 1181.

However, the present invention is not limited to this embodiment. For example, in another embodiment, there can be only one first auxiliary contact having one fifth pad portion exposed on the third side of the second circuit board, and one first cooperating contact electrically connected to and affixed with the fifth pad portion. Alternatively, in another embodiment, there can be no passive electronic component or two passive electronic components located at the third side and the fourth side of the second circuit board.

In addition, as shown in FIG. 2 to FIG. 9, in this embodiment, the image capturing assembly 11 further includes a flexible auxiliary circuit board 119 and two light emitting components 11A. The two light emitting components 11A are disposed on the flexible auxiliary circuit board 119 and configured to emit light. The flexible auxiliary circuit board 119 is affixed with and electrically connected to the second circuit board 113.

Specifically, the second circuit board 113 can include two second auxiliary contacts 1136. Each of the second auxiliary contacts 1136 can include a sixth pad portion 1136A. The two sixth pad portions 1136A can be located on two lateral sides of the second circuit board 113 which are opposite to each other and adjacent to the third side 1132 and the fourth side 1133 of the second circuit board 113. The flexible auxiliary circuit board 119 can include two second cooperating contacts 1191 electrically connected to the two light emitting components 11A. Each of the second cooperating contacts 1191 can include a seventh pad portion 1191A. Each of the seventh pad portions 1191A can be perpendicular to and affixed with the sixth pad portion 1136A by soldering, i.e., the image capturing assembly 11 can further include two fourth soldering structures 11B, and each of the fourth soldering structures 11B is connected between the corresponding sixth pad portion 1137A and the corresponding seventh pad portion 1191A.

However, the present invention is not limited to this embodiment. For example, in another embodiment, there can be one flexible auxiliary circuit board and one light emitting component. Alternatively, there can be no flexible auxiliary circuit board and no light emitting component.

Figure 10:
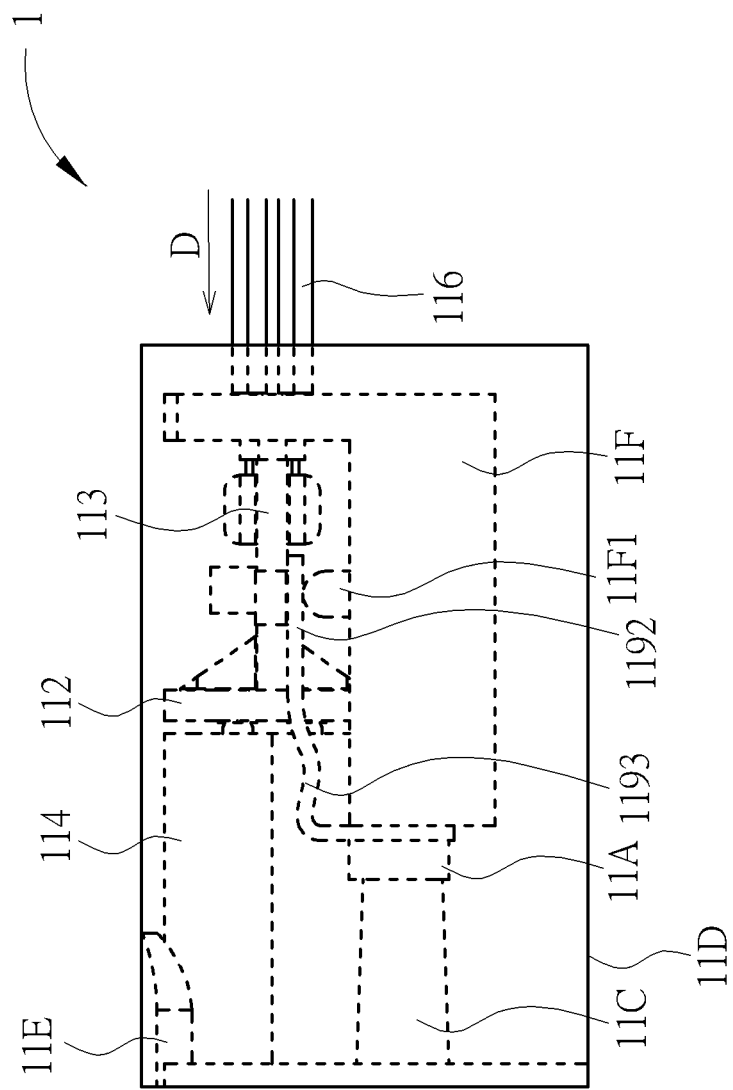
FIG. 10 is a partial lateral view of the endoscope according to the embodiment of the present invention.

Please refer to FIG. 2, FIG. 3, FIG. 6, FIG. 7 and FIG. 10. FIG. 10 is a partial lateral view of the endoscope 1 according to the embodiment of the present invention. As shown in FIG. 2, FIG. 3, FIG. 6, FIG. 7 and FIG. 10, the image capturing assembly 11 further includes two light guiding components 11C, a shell 11D, a window 11E and a mounting base 11F. The two light guiding components 11C are disposed on the shell 11D and configured to guide the light emitted from the two light emitting components 11A. The window 11E is disposed on the shell 11D and configured to protect internal components, such as the lens assembly 114 and the two light guiding components 11C, from being damaged. The window 11E includes an objective lens 11E1 and two light guiding lenses 11E2. The objective lens 11E1 is configured to receive light from an observed object and the light from the observed object can pass through the objective lens 11E1 and travel toward the lens assembly 114. The two light guiding lenses 11E2 are connected to the two light guiding components 11C respectively and configured to receive light from the two light guiding components 11C respectively, and the light from the two light guiding components 11C can pass through the two light guiding lenses 11E2 respectively and travel toward the observed object. The mounting base 11F is slidably installed inside the shell 11D for driving at least the first circuit board 112, the second circuit board 113, the image sensing device 111, the lens assembly 114, the flexible auxiliary circuit board 119 and the two light emitting components 11A to slide together with the mounting base 11F.

Specifically, in this embodiment, the flexible auxiliary circuit board 119 can include a main body 1192 and two resilient arms 1193 extending from the main body 1192. Each of the resilient arms 1193 includes a spring structure arrange along a plane parallel to the main body 1192. The two light emitting components 11A can be disposed on the two resilient arms 1193. The mounting base 11F can be adhered with the two resilient arms 1193 by adhesives, e.g., UV glue. Each of resilient arms 1193 is configured to bias the light emitting components 11A to abut against the corresponding light guiding component 11C. A supporting structure 11F1 can be formed on the mounting base 11F, and the flexible auxiliary circuit board 119 is located between and abutted by the supporting structure 11F1 and the second circuit board 113.

However, the present invention is not limited to this embodiment. For example, in another embodiment, there can be a plurality of supporting structures formed on the mounting base, and one light guiding component disposed on the shell.

As shown in FIG. 2, FIG. 3, FIG. 6, FIG. 7 and FIG. 10, during assembly of the image capturing assembly 11, the mounting base 11F can be pushed to slide into the shell 11D along a sliding direction D to push the two resilient arms 1193 of the flexible circuit board 119 to drive the first circuit board 112, the second circuit board 113, the image sensing device 111, the lens assembly 114, the flexible auxiliary circuit board 119, the two light emitting components 11A and the five cables 116 to slide together until the two light emitting components 11A abut against the two light guiding components 11C respectively. Specifically, the spring structures of the two resilient arms 1193 provide elasticity on the sliding direction D during assembly of the image capturing assembly 11. When the two light emitting components 11A abut against the two light guiding components 11C respectively, the two light emitting components 11A can be adhered with the two light guiding components 11C respectively by adhesives, e.g., UV glue, and then the lens assembly 114 can further be driven to slide along the sliding direction D to abut against the window 11E by pushing the first circuit board 112, the second circuit board 113 or the cables 116. During the aforementioned sliding movement of the lens assembly 114 along the sliding direction D, since the main body 1192 of the flexible circuit board 119 can be driven to slide along the sliding direction D together with the second circuit board 113, the resilient arms 1193 of the flexible circuit board 119 can be resiliently deformed to generate resilient forces for driving the two light emitting components 11A to abut against the two light guiding components 11C, which prevents light leakage caused by separation of the light guiding component 11C and the light emitting component 11A. When the lens assembly 114 abuts against the window 11E, the lens assembly 114 can be adhered with the window 11E by adhesives, e.g., UV glue.

Moreover, it should be noticed that the image capturing assembly 11 also can be used in another image capturing apparatus, e.g., a microscope.

In contrast to the prior art, the present invention utilities the first circuit board for mounting the image sensing device and further utilizes the second circuit board affixed with and substantially perpendicular to the first circuit board for establishing an electrical connection between the second contact of the second circuit board and the electrical connecting component via the first contact of the first circuit board. The aforementioned configuration of the present invention is space-saving. Therefore, the present invention has advantages of compact structure and small size. Besides, when there are a plurality of electrical connecting components, a plurality of first contacts and a plurality of second contacts, the electrical connecting components of the image sensing device can be electrically connected to the second contacts of the second circuit board by the first contacts of the first circuit board respectively, wherein a layout or an arrangement of the electrical connecting components is different from a layout or an arrangement of the second contacts. Therefore, it facilitates adaptation and modularization.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An image capturing assembly comprising:
    an image sensing device comprising at least one electrical connecting component;
    a first circuit board comprising at least one first contact, the image sensing device being mounted on the first circuit board, and the at least one electrical connecting component being electrically connected to the at least one first contact;
    a second circuit board comprising at least one second contact, the second circuit board being affixed with the first circuit board and perpendicular to the first circuit board, and the at least one second contact being electrically connected to the at least one first contact, so that the at least one second contact is electrically connected to the at least one electrical connecting component by the at least one first contact;
    a lens assembly assembled with the image sensing device;
    a flexible auxiliary circuit board comprising a main body and at least one resilient arm extending from the main body;
    at least one light emitting component disposed on the at least one resilient arm and configured to emit light; and
    at least one light guiding component configured to guide the light emitted from the at least one light emitting component, the at least one light emitting component being biased to abut against the at least one light guiding component by the at least one resilient arm.

2. The image capturing assembly of claim 1, wherein a pad portion of the at least one first contact is affixed with a pad portion of the at least one second contact by a soldering structure connected between the pad portion of the at least one first contact and the pad portion of the at least one second contact.

3. The image capturing assembly of claim 2, wherein the pad portion of the at least one first contact and the pad portion of the at least one second contact are perpendicular to each other.

4. The image capturing assembly of claim 1, further comprising at least one cable electrically connected to the second circuit board.

5. The image capturing assembly of claim 4, wherein the second circuit board further comprises at least one third contact electrically connected to the at least one second contact, and the at least one cable is affixed with and electrically connected to the at least one third contact, so that the at least one cable is electrically connected to the at least one electrical connecting component by the at least one third contact, the at least one second contact and the at least one first contact.

6. The image capturing assembly of claim 1, further comprising a shell, a window and a mounting base, the window being disposed on the shell, the mounting base being slidably installed inside the shell, the first circuit board, the second circuit board, the image sensing device, the lens assembly, the flexible auxiliary circuit board and the at least one light emitting component being slidable together with the mounting base, and the at least one resilient arm being resiliently deformed to drive the at least one light emitting component to abut against the at least one light guiding component when the lens assembly slides to abut against the window.

7. The image capturing assembly of claim 6, wherein at least one supporting structure is formed on the mounting base, and the flexible auxiliary circuit board is located between and abutted by the at least one supporting structure and the second circuit board.

8. The image capturing assembly of claim 1, wherein the flexible auxiliary circuit board is affixed with and electrically connected to the second circuit board.

9. The image capturing assembly of claim 8, wherein the second circuit board comprises at least one auxiliary contact, the flexible auxiliary circuit board comprises at least one cooperating contact electrically connected to the at least one light emitting component, a portion of the at least one auxiliary contact is located on a lateral side of the second circuit board, the at least one cooperating contact is affixed with and electrically connected to the at least one auxiliary contact.

10. The image capturing assembly of claim 9, wherein the portion of the at least one auxiliary contact and a portion of the at least one cooperating contact are perpendicular to each other.

11. The image capturing assembly of claim 1, further comprising at least one passive electronic component electrically connected to the second circuit board.

12. The image capturing assembly of claim 11, wherein the second circuit board comprises at least one auxiliary contact, the at least one passive electronic component comprises at least one cooperating contact, a portion of the at least one auxiliary contact is located on a side of the second circuit board, and the at least one cooperating contact of the at least one passive electronic component is affixed with and electrically connected to the at least one auxiliary contact.

13. An endoscope comprising:
 a flexible tube; and
 an image capturing assembly connected to the flexible tube and comprising:
  an image sensing device comprising at least one electrical connecting component;
  a first circuit board comprising at least one first contact, the image sensing device being mounted on the first circuit board, and the at least one electrical connecting component being electrically connected to the at least one first contact;
  a second circuit board comprising at least one second contact, the second circuit board being affixed with the first circuit board and perpendicular to the first circuit board, and the at least one second contact being electrically connected to the at least one first contact, so that the at least one second contact is electrically connected to the at least one electrical connecting component by the at least one first contact;
  a lens assembly assembled with the image sensing device;
  a flexible auxiliary circuit board comprising a main body and at least one resilient arm extending from the main body;
  at least one light emitting component disposed on the at least one resilient arm and configured to emit light; and
  at least one light guiding component configured to guide the light emitted from the at least one light emitting component, the at least one light emitting component being biased to abut against the at least one light guiding component by the at least one resilient arm.

14. The endoscope of claim 13, wherein the image capturing assembly further comprises a shell, a window and a mounting base, the window is disposed on the shell, the mounting base is slidably installed inside the shell, the first circuit board, the second circuit board, the image sensing device, the lens assembly, the flexible auxiliary circuit board and the at least one light emitting component are slidable together with the mounting base, and the at least one resilient arm is resiliently deformed to drive the at least one light emitting component to abut against the at least one light guiding component when the lens assembly slides to abut against the window.

15. The endoscope of claim 13, wherein the flexible auxiliary circuit board is affixed with and electrically connected to the second circuit board, the second circuit board comprises at least one auxiliary contact, the flexible auxiliary circuit board comprises at least one cooperating contact electrically connected to the at least one light emitting component, a portion of the at least one auxiliary contact is located on a lateral side of the second circuit board, the at least one cooperating contact is affixed with and electrically connected to the at least one auxiliary contact.

* * * * *